United States Patent
Berretta

(10) Patent No.: US 9,040,758 B2
(45) Date of Patent: May 26, 2015

(54) WASHING SYSTEM FOR NITROAROMATIC COMPOUNDS

(75) Inventor: Sergio Berretta, Vancouver (CA)

(73) Assignee: NORAM INTERNATIONAL LIMITED (IE)

( * ) Notice: Subject to any disclaimer, the term of this patent is extended or adjusted under 35 U.S.C. 154(b) by 499 days.

(21) Appl. No.: 13/388,836

(22) PCT Filed: Aug. 18, 2009

(86) PCT No.: PCT/IB2009/006570
§ 371 (c)(1),
(2), (4) Date: Feb. 3, 2012

(87) PCT Pub. No.: WO2011/021057
PCT Pub. Date: Feb. 24, 2011

(65) Prior Publication Data
US 2012/0136181 A1    May 31, 2012

(51) Int. Cl.
| C07C 27/26 | (2006.01) |
| C07C 201/16 | (2006.01) |
| C02F 1/04 | (2006.01) |
| C02F 1/20 | (2006.01) |
| C02F 101/38 | (2006.01) |

(52) U.S. Cl.
CPC ............. C07C 201/16 (2013.01); C02F 1/04 (2013.01); C02F 1/20 (2013.01); C02F 2101/38 (2013.01); C02F 2209/06 (2013.01)

(58) Field of Classification Search
CPC ............................. C07C 201/16; C07C 205/06
USPC ............................................ 568/958
See application file for complete search history.

(56) References Cited

U.S. PATENT DOCUMENTS

| 3,936,360 A | 2/1976 | Chih Wu |
| 4,371,731 A | 2/1983 | Washer |
| 4,604,214 A | 8/1986 | Carr et al. |
| 4,925,565 A | 5/1990 | Adams et al. |
| 5,124,026 A | 6/1992 | Taylor et al. |
| 5,763,696 A | 6/1998 | Quakenbush et al. |
| 5,820,764 A | 10/1998 | Joulak et al. |
| 6,288,289 B1 | 9/2001 | Boyd et al. |

(Continued)

FOREIGN PATENT DOCUMENTS

EP    1 593 654 A1    11/2005

OTHER PUBLICATIONS

Booth, G., "Nitro Compounds, Aromatic", in "Ullmann's Encyclopedia of Industrial Chemistry, 7th Ed.", Wiley-VCH Verlag GmbH & Co. KGaA, Weinheim, (2005), p. 1-47.

(Continued)

*Primary Examiner* — Jafar Parsa
(74) *Attorney, Agent, or Firm* — McKee, Voorhees & Sease, P.L.C.

(57) ABSTRACT

A method of removing alkalinity and salt from a nitroaromatic product downstream of water washing to remove mineral acids and alkaline washing to remove salts of organic acids, comprises washing the product stream with an acidic aqueous solution, prior to the step of removing excess organic reactant, by steam stripping or distillation. Acid removed from the stripper or column is recycled back for use in the acidic washing. The acidic washing is done instead of the neutral washing step of the prior art. It removes residual salt and decreases the level of entrained colloidal water in the nitroaromatic product.

35 Claims, 3 Drawing Sheets

(56) References Cited

U.S. PATENT DOCUMENTS

| | | | |
|---|---|---|---|
| 6,506,948 B1 * | 1/2003 | Sawicki | 568/934 |
| 7,326,816 B2 | 2/2008 | Knauf et al. | |
| 7,344,650 B2 | 3/2008 | Knauf et al. | |
| 7,470,826 B2 | 12/2008 | Hermann et al. | |
| 2007/0088183 A1 * | 4/2007 | Hermann et al. | 568/927 |

OTHER PUBLICATIONS

Dunlap, K.L., "Nitrobenzene and Nitrotoluenes", "Kirk-Othmer Encyclopedia of Chemical Technology, vol. 15", John Wiley & Sons, Inc., (1981) p. 916-32.

Dugal, M., "Nitrobenzene and Nitrotoluenes", "Kirk-Othmer Encyclopedia of Chemical Technology, vol. 17", John Wiley & Sons, Inc., (2005), p. 1-30.

Guenkel, A.A., "Nitrobenzene and Nitrotoluene", in J.J. McKetta and W.A. Cunningham (Eds.), "Encyclopedia of Chemical Processing and Design", Marcel Dekker (1990) p. 165-188.

Gustin, J.-L., "Runaway Reaction Hazards in Processing Organic Nitro Compounds", Organic Proc. Res. & Dev., 2 (1998) p. 27-33.

Hermann, H. et al., "Industrial Nitration of Toluene to Dinitrotoluene", in L.F. Albright, "Nitration, Recent Laboratory and Industrial Development", ACS Symposium Series 623, American Chemical Society, Washington, D.C., (1996), p. 234-249.

Noram International Limited, PCT/IB2009/006570, filed Aug. 18, 2009, "Written Opinion of the International Searching Authority", mailed Feb. 18, 2012.

* cited by examiner

WASHING SYSTEM FOR NITROAROMATIC COMPOUNDS

CROSS-REFERENCE TO RELATED APPLICATIONS

This is a National Phase application claiming priority to PCT/IB2009/006570 filed Aug. 18, 2009 of which is herein incorporated by reference in its entireties.

BACKGROUND OF THE INVENTION

The invention pertains to a process for washing nitroaromatic products to remove impurities.

In the industrial production of nitrocompounds, such as mononitrobenzene or nitrotoluene, significant amounts of acidic organic by-products are formed. In mononitrobenzene production the main by-product species are nitrophenols (i.e., an organic acid), and in nitrotoluene production they are nitrocresols. Other minor organic by-product impurities are also present. In addition to by-products, other impurities present in the nitrated product are sulfuric acid catalyst and unreacted starting reactants such as benzene, in the mononitrobenzene product, or toluene, in the nitrotoluene product.

The organic acid by-products present in the crude product stream are particularly undesirable since they can adversely affect later users of the products (i.e., use in other processes, such as in the production of aniline in the case of nitrobenzene). The contaminants are therefore typically removed through a series of process steps. These process steps have been described both in the prior art patents and in the literature, e.g., U.S. Pat. No. 6,288,289 Boyd et al.; U.S. Pat. No. 7,326,816 Knauf et al.; U.S. Pat. No. 7,344,650 Knauf et al.; U.S. Pat. No. 7,470,826 Hermann et al.;. K. L. Dunlap, "Nitrobenzene and Nitrotoluenes", "Kirk-Othmer Encyclopedia of Chemical Technology, Vol. 15", John Wiley & Sons, Inc., (1981) 916-32; M. Dugal, "Nitrobenzene and Nitrotoluenes", "Kirk-Othmer Encyclopedia of Chemical Technology, Vol. 17", John Wiley & Sons, Inc., (2005) on-line; A. A. Guenkel, "Nitrobenzene and Nitrotoluene", in J. J. McKetta and W. A. Cunningham (Eds.), "Encyclopedia of Chemical Processing and Design", Marcel Dekker (1990); J.-L. Gustin, "Runaway Reaction Hazards in Processing Organic Nitro Compounds", Organic Proc. Res. & Dev., 2 (1998) 27-33; H. Hermann et al., "Industrial Nitration of Toluene to Dinitrotoluene", in L. F. Albright, "Nitration, Recent Laboratory and Industrial Development", ACS Symposium Series 623, American Chemical Society, Washington, D.C., (1996) 234-249; G. Booth, "Nitro Compounds, Aromatic", in "Ullmann's Encyclopedia of Industrial Chemistry, 7th Ed.", Wiley-VCH Verlag GmbH & Co. KGaA, Weinheim, (2005).

The typical prior art steps for removing product impurities from the stream of nitrated product comprise the steps of water washing, alkaline washing and neutral washing.

The initial step of water washing uses water as the washing liquid and removes inorganic acids, such as sulfuric acid. The acids can be removed with a selectivity that can be adjusted by those knowledgeable in the art to tailor the resultant waste streams (i.e., water waste) and downstream caustic consumption rates with a particular plant's requirements. (The water washing step is sometimes referred to in the art as "acid washing," because it removes acid. In the present specification, it is referred to as "water washing," meaning the washing of the product stream with water for the purpose of removing mineral acids.) The corresponding apparatus in which this step is conducted is referred to herein as a "water washer."

Following the water washing step, organic by-products are extracted from the nitrated organic product by washing it with an aqueous alkaline solution. The base is typically, but is not limited to, sodium hydroxide, sodium carbonate or ammonia. Through this washing step, referred to herein as "alkaline washing," the acidic organic by-products, which are dissolved in the organic product phase, are neutralized by the base and to converted to organic salts, which readily transfer into the aqueous washing solution. To achieve industry-accepted product specifications for the acidic organic by-products, more than one stage of alkaline washing is typically used. The corresponding apparatus in which this washing step is conducted is referred to herein as an "alkaline washer."

The above-described washing steps are carried out by mixing the two immiscible fluids together to transfer the target compounds from one phase to the other, followed by settling of the mixture back into two phases to allow separation and recovery of the two fluids. These can be single or multiple units, where multiple units can be arranged in cross-flow or more commonly a counter-current flow pattern and some degree of recycling/recirculating of the wash solutions, within each unit, is typically practiced.

The organic product leaving the alkaline washing step typically carries with it a small amount of the base (e.g., sodium hydroxide) used in the extraction, and a small amount of the salt formed in the alkaline washer (e.g., sodium nitrophenolates in the case of nitrobenzene production). More specifically, this residual salt is carried by small water droplets entrained in the organic product leaving the alkaline washing step, rather than by the organic product itself. As discussed below, this entrained salt, if not properly removed, can present a significant challenge in the operation of the downstream equipment. To minimize the effect of salt carry-over, one or more "neutral washers" (i.e., salt-removal washers) downstream of the alkaline washers are used. In this specification, the term "neutral washing" refers to washing the nitrated product stream with water to remove salts. The water has a substantially neutral pH. Multiple units can be used, operated in cross-flow or counter-current-flow arrangements. The wastewater from these units can be introduced into the upstream alkaline washing step to recycle the recovered alkaline salt.

Having removed inorganic acids (i.e., in the water washer), organic acids (i.e., in the alkaline washer) and hydroxyl-nitroaromatics (i.e., in the neutral washer), the next step is to remove residual organic reactant. Some of the reactions to produce nitroaromatics are run with an excess of the organic feed reactant. For the example of mononitrobenzene, excess benzene is used, which remains in the crude product stream. Therefore, the product leaving the washing train is typically sent, directly or indirectly, to either a stripper or a distillation column to recover the excess organic reactant, which up to this point in the process remains in solution with the nitrated product.

In a live steam stripper, the excess organic feed reactant is stripped and removed through the top of the column, then condensed and recycled back to the process reactor. The nitrated product leaves the bottom of the column together with any steam condensed in the column. Within the column, entrained caustic, or other salts, in the nitrated product fed to the stripper is transferred to the water condensate. Outside the column, the nitrated product is separated from the condensate and sent to the downstream process plant. In the case of the mononitrobenzene process, the downstream process plant would typically be aniline production. The product mononitrobenzene leaving the plant typically carries with it a small amount of entrained water condensate which contains some of the sodium hydroxide, or salts, present in the feed to the stripper. This sodium hydroxide, or salt, eventually ends up in the downstream aniline process reactor and is suspected of negatively affecting the activity of its catalyst.

A distillation column can also be used instead of a steam stripper to remove excess organic feed reactant from the nitrated product. The main operating difference from steam stripping is that, in a distillation column, heat is introduced indirectly via a reboiler. As a result, no water condensate forms in the column and a "dry" nitrated product is obtained. Without water in the final product, salts that were dissolved in the water entrained with the organic product feed to the column precipitate out, leading to plugging of the column or downstream equipment. Some of this precipitate is carried all the way through with the nitrated product into the downstream process.

Thus it is very important to ensure the removal of salts from the nitrated product before the stripping or distillation steps, underlining the importance of the proper operation of the neutral (salt removal) washing step. In some nitrations, this proper operation becomes critical if very pure product is required, because then the process would typically include a further distillation step downstream of the benzene recovery column. This involves a second distillation column, operating at a higher temperature than the column for the removal of excess reactant, where heavy components are distilled out. In such a case, un-removed residual salts can lead to chemical instabilities, within the column, with hazardous results.

In general, properly designed neutral washers are very effective in removing entrained salt from the nitrated product. However, neutral washers are also operationally sensitive. This sensitivity is exhibited by a tendency of the two phases (i.e., water and nitrated product) in the washing operation to form one relatively emulsified phase that does not properly settle out into the two phases. The resulting effect is that excessive water can be carried over into the downstream unit operations, which can lead to production shutdowns. This formation, of a single emulsified phase, can occur if the operation on the washer/separator is allowed to drift out of design conditions (e.g., flow rates, mixing intensity, temperature, etc.). It also tends to occur more frequently as one pushes the neutral washer to ever cleaner product, for example by using more than one neutral washer in counter-current flow mode or a larger flow of water in a single neutral washer. Either one of the latter two conditions is desired to achieve significant salt extraction but they are typically not practical without costly separation enhancing equipment such as electrophoresis or coalescers.

Even when good separation of the two fluids (i.e., water and nitrated product) occurs within the neutral washer, whether or not enhanced by for example a coalescer, there is still a significant amount of water entrainment with the exiting product, visible by the cloudy or milky appearance of the nitrated product. This appearance is due to water present, as a "colloidal" stable form, in the product. As noted above, it is the entrained water that carries the bulk of the salt entrained in the nitrated product leaving the neutral washing stage. This concentration of "colloidal" water droplets in the product cannot be easily decreased under the typical operating conditions of the neutral washer. This field observation (i.e., the existence of a minimum achievable water entrainment) has been confirmed in to laboratory experiments. This entrained colloidal water typically amounts to around 1 wt % of the nitrated product leaving a neutral washer, and contains a residual fraction of the dissolved salts in the water used in the washing step. The latter issue leads to design and operating constraints, for example, the provision for excess equipment capacity installation to is achieve desired salt level in the nitrated product.

SUMMARY OF THE INVENTION

The invention provides a method for removing impurities from a product stream comprising a nitroaromatic product. The method comprises the step of washing the product with an acidic aqueous solution. The step may be carried out downstream of water washing and alkaline washing, to remove alkalinity and salt from the nitroaromatic product.

According to some embodiments, the method includes removing residual organic reactant by steam stripping or distillation, downstream of the washing step. Acid from the steam stripping or distillation may be recycled for use in the step of washing with acidic aqueous solution.

The invention also provides an apparatus for carrying out the method of the invention. The apparatus comprises an acidic salt-removal washer downstream of a water washer and an alkaline washer.

These and other features of the invention will be apparent from the following description and drawings of particular embodiments.

DETAILED DESCRIPTION OF THE INVENTION

Figure 1:
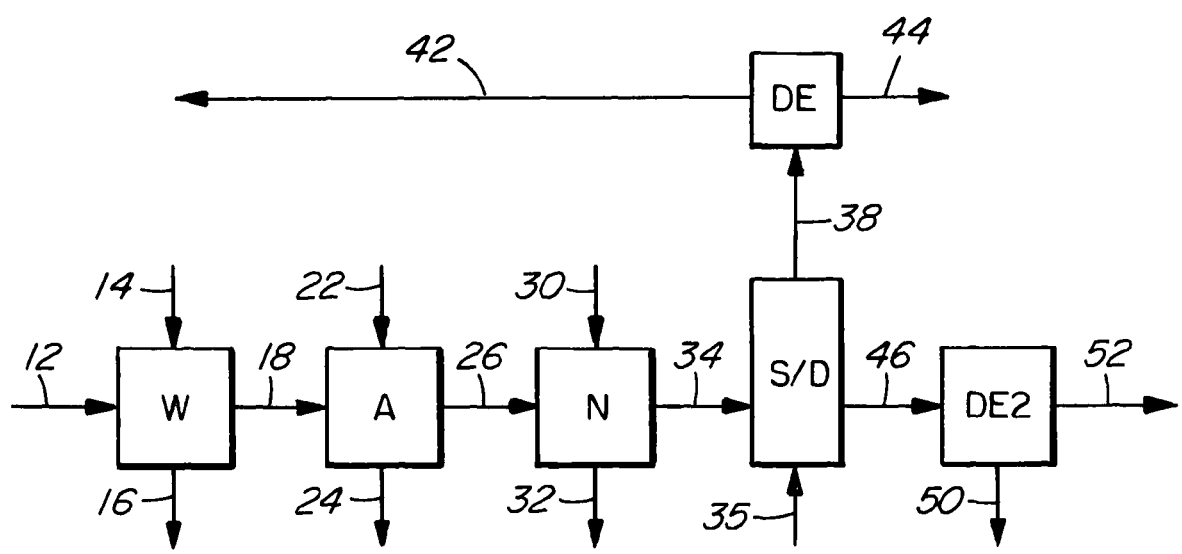
FIG. 1 is a schematic diagram of the process of a prior art system for washing nitrated products.

In the following description and in the drawings, corresponding and like elements are referred to by the same reference characters.

The process of the invention is best understood by comparison with the typical prior art washing process. As illustrated in FIG. 1, and as explained in greater detail above, the prior art process is essentially as follows. A water washer W receives a stream of nitrated product (stream 12) from an upstream nitrator (not shown). Water (stream 14) is fed into the water washer W. An aqueous solution of mineral acids (stream 16) is removed from the water washer and the washed product (stream 18) is fed to the alkaline washer A. An alkaline washing solution (stream 22) is fed into the alkaline washer A. An aqueous solution of the salts of organic acids (stream 24) is removed and the washed product (stream 26) is fed to the neutral washer N. Water (stream 30) is fed into the neutral washer N. The waste stream 32 is removed and the washed product stream 34 is fed to a distillation column or steam stripper S/D. Steam or heat (stream 35) is is fed to the bottom of the stripper or distillation column, respectively. The residual organic reactant and water (stream 38) are removed from the top of the distillation column or stripper S/D and fed to a decanter DE, where the organic reactant is separated from the water. The reactant (stream 42) is fed back to the nitrator and the water (stream 44) is removed. Cleaned nitrated product (stream 46) is removed from the distillation column or steam stripper S/D. Where the apparatus has a steam stripper, the nitrated product stream 46 is fed to an additional decanter DE2 for removal of condensed water (stream 50) to produce the final cleaned product (stream 52).

In the invention, an acidic aqueous solution is used to wash the product stream to remove alkalinity and salts. This wash is done instead of (or in some embodiments, in addition to) the neutral washing step of the prior art process, following the water washing and the alkaline washing steps, and prior to the step of removing residual organic reactant.

The inventor has determined that adding a small amount of acid to a neutral washer significantly improves its performance (note that the added acid mainly dissolves in the aqueous phase and not in the nitrated product). The residual salt in the nitrated product is more effectively removed and the washers show a greater resistance to the formation of phase emulsions. Further, the inventor has determined that the level of entrained colloidal water, the main carrier of salt in the nitrated product, is greatly decreased.

Figure 2:
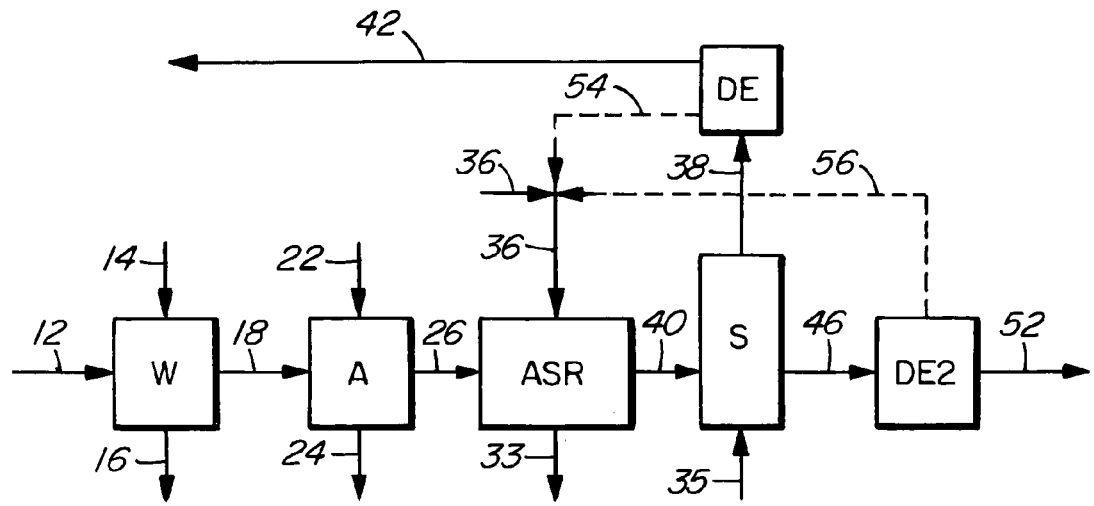
FIG. 2 is a schematic diagram of an embodiment of the invention, which uses a steam stripper.

Referring first to FIG. 2, which depicts an embodiment of the invention where the washing stages are followed by steam stripping, the step of washing the nitrated product stream with an acidic aqueous solution is carried out downstream of the water washer W and the alkaline washer A, in the acidic salt-removal washer ASR. The apparatus upstream of the acidic salt-removal washer is the same as that upstream of the neutral washer N in the prior art process of FIG. 1, as described above, with the nitrated product stream 12 being first water washed and then alkaline washed, before being washed with an acidic aqueous solution in the acidic salt-removal washer ASR. Structurally, the acidic salt-removal washer is the same as the prior art neutral washer N, but the washing fluid fed to it is acidic aqueous solution (stream 36) rather than substantially neutral water. A solution of salts from the neutralization of residual alkalinity (stream 33) is removed from it. This stream could be recycled to the alkaline washing. The acidic salt-removal washer can be a single unit or multiple units, where multiple units can be operated in cross-current flow, co-current flow or counter-current flow arrangements.

After acid washing, the nitrated product (stream 40) is fed to the steam stripper S. Depending on its volatility (i.e., its ease to evaporate relative to the nitrated product), traces of the added acid will appear in the aqueous phase that appears with the condensed recovered organic reactant at the top of the stripper (stream 38) and/or in the aqueous phase that appears with the clean product at the bottom of the stripper (stream 46). These aqueous streams (stream 54 from the decanter DE and stream 56 from the additional decanter DE2), which contain some of the added acid, can be recycled back to the acidic salt-removal washer ASR to decrease the requirement for make-up acid. While this approach does involve the clean product being in contact with a small amount of an acid, this is largely is offset by the lower carryover of water entrainment in the nitrated product. The operational performance and reliability of the final washing step (i.e., the salt removal stage) is also significantly improved, leading to more stable plant operation and decreased requirement for the provision of excess equipment capacity.

Figure 3:
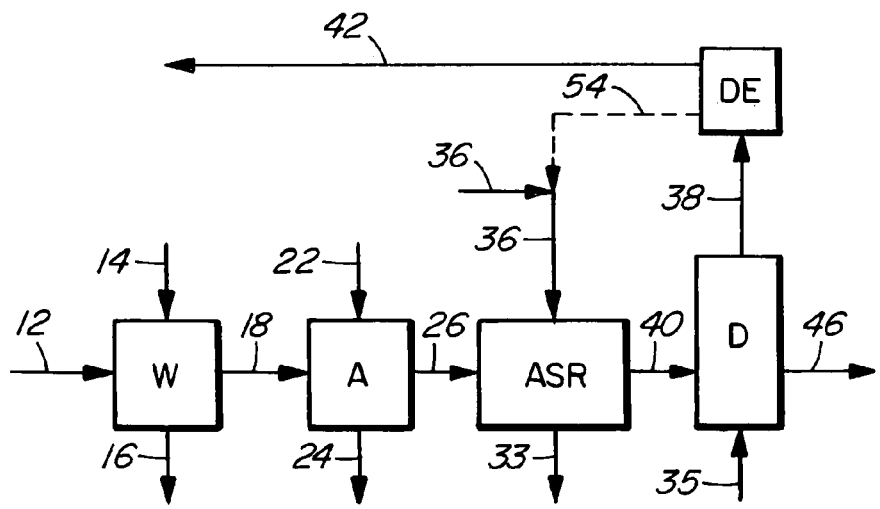
FIG. 3 is a schematic diagram of an embodiment of the invention, which uses a distillation column.

FIG. 3 depicts an embodiment of the invention where the washing stages are followed by a distillation column D rather than a steam stripper. The residual organic reactant and water (stream 38) are removed from the top of the distillation column and fed to the decanter DE. Water and acid removed in the decanter are fed back to the acidic salt-removal washer (stream 54).

If the acid used is chosen to be a volatile acid (i.e., an acid that evaporates more readily compared to the nitrated organic product), a large part of the acid ends up at the top of the stripper, in the embodiment of FIG. 2. Where the washing stages are followed by distillation, as in the embodiment of FIG. 3, then all the volatile acid ends up at the top of the column. In the latter case a volatile acid must be used or acid ends up with the nitrated product leaving the column. The reason is that in a distillation column, in contrast to a live steam stripper, there is no water exiting the bottom of the column.

In choosing a volatile acid for use in this invention, the preferred acid is nitric acid because it is already present in the nitration plants. However, the invention is not limited to the type of acid that can be used. Where a live steam stripper is used to remove the excess reactant from the nitrated product, the added acid does not need to be a volatile acid. Hence an acid such as sulfuric acid could be used. If volatile acids are used, such acids can also include formic acid, oxalic acid and nitrous acid. Sufficient acid is used in the acidic salt-removal washing stage to maintain a pH below 6, alternatively below 5.

An additional benefit is provided when recycling the volatile acid recovered at the top of the distillation column D as shown by the dashed line in FIG. 3 (stream 54). During operation, the acidic salt-removal washer can be operated with pH values as low as 2 to 3, with far less make-up acid than might be expected. It is hypothesized that an additional fortuitous source of acid is present, thought to be due to traces of dissolved NO in the washed mononitrobenzene. Such dissolved NO would be stripped in the distillation column and react with oxygen to make $NO_2$. The $NO_2$ is absorbed by the water stripped from the product and condensed in the distillation column condenser where it reacts with the water to form nitric acid and nitrous acid. A similar benefit would be expected on recycling water collected from the top of the steam stripper in FIG. 2 (stream 54). Thus, while many sources of acid could be envisioned to be used to implement the step of washing with an acidic aqueous solution of the invention, the preferred source is recovered acid solution from the top of either the organic reactant recovery distillation column or steam stripper.

In general, the washing efficiency of counter-current washers is significantly affected by the entrainment rate of aqueous solution in the forward moving nitrated product. Depending on the aqueous solution addition rate, even an entrainment rate of 0.5 wt % of free aqueous phase in is the nitrated product can double the number of washing stages required to achieve a typical targeted salt carry-over specification. As a result, the discovery that the use of an acidic salt-removal washing stage decreases the minimum stable water entrainment in the nitrated product fed to the stripper or distillation column down to approximately 0.04 wt % can provide a substantial benefit. For example, it can allow a reduction on the number of washer/separators, providing a capital investment savings in new nitration plants.

As explained above, operating experience has shown that neutral washers, operated at pH close to neutral, tend to emulsify even under minor plant upsets. As a result, the method of the invention, which has the acidic salt-removal washer operating at low pH, also greatly reduces the potential for the formation of emulsions that are experienced with neutral washers. This provides an operating cost advantage by reducing unexpected plant shutdowns, and, for new nitration plants, it can decrease the requirement for the provision of excess equipment capacity.

The benefits of washing with acidic aqueous solution are not limited to an application where the upstream washing system comprises a water washer followed by an alkaline washer. It also applies to the case where the upstream washing system comprises only an alkaline washer, without a preceding water washer. It also applies to the case where neutral washers are used with either of these combinations.

Figure 4:
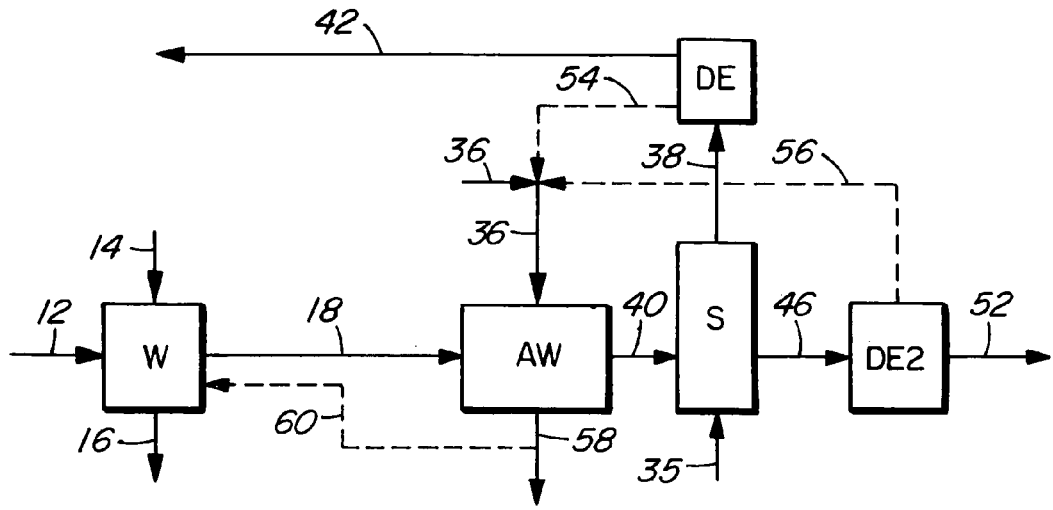
FIG. 4 is a schematic diagram of a further embodiment of the invention, which uses a steam stripper and has no alkaline wash.
Figure 5:
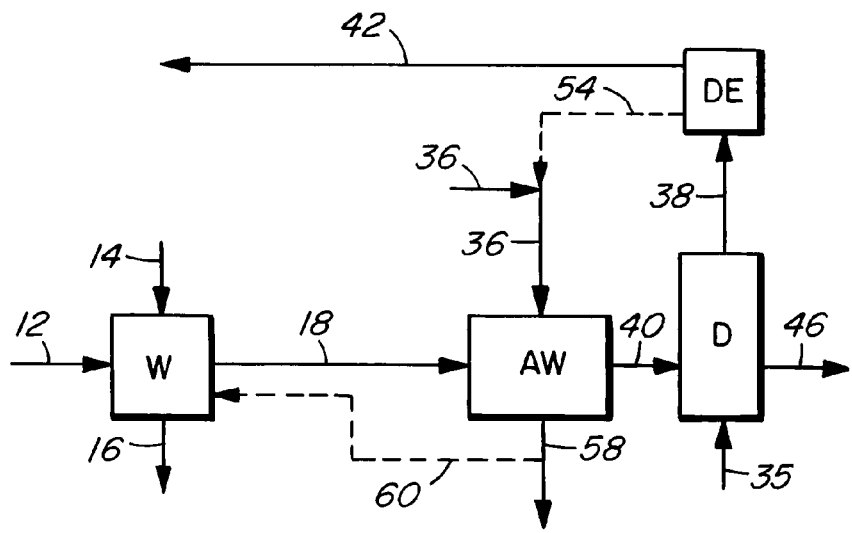
FIG. 5 is a schematic diagram of a further embodiment of the invention, which uses a distillation column and has no alkaline wash.

FIGS. 4 and 5 illustrate further embodiments of the invention, in which the upstream washing system comprises one or more water washers is W and does not include an alkaline washer. Here, the step of washing the product (stream 18) with an acidic aqueous solution (stream 36) removes hydrophilic acids, such as sulfuric acid or oxalic acid, from the nitrated product. The acidic solution leaving the acidic washer AW (stream 58) can be recycled back to the water washer W (stream 60). FIG. 4 shows the arrangement where a steam stripper S is used following the acidic wash and FIG. 5 the arrangement where a distillation column D is used. Acid removed from the stripper or column is recycled back to the acidic washer. The acids and pHs used are the same as those described above for the FIGS. 2 and 3 embodiments.

EXAMPLE

The invention in accordance with the embodiment of FIG. 3 was tested in a mononitrobenzene production facility using nitric acid. The facility used a distillation column to recover benzene dissolved in the product. Any water and volatile acid stripped out of the mononitrobenzene product in the distillation column was condensed, separated from the recovered benzene and recycled back to the acidic salt-removal washer. A substantial decrease in the level of entrained colloidal water in the mononitrobenzene leaving the acidic salt-removal washer was found, dropping from 1 wt % in a typical neutral washer with no acid addition, to below 0.04 wt %. The washing system did not experience an emulsification upset in the acidic salt-removal washer during over five months of operation.

Although the invention has been described in terms of various embodiments, it is not intended that the invention be limited to these embodiments. Various modifications within the scope of the invention will be apparent to those skilled in the art. The scope of the invention is defined by the claims that follow.

What is claimed is:

1. A method of removing impurities from a product stream comprising a nitroaromatic product, comprising the steps of:
   (a) alkaline washing the nitroaromatic product stream to remove acidic organic by-products; and
   (b) washing the nitroaromatic product stream from step (a) with an acidic aqueous solution.

2. A method according to claim 1, further comprising the step of water washing the product stream upstream of step (a) to remove mineral acids.

3. A method according to claim 1, further comprising the step of (c) removing residual organic reactant from the product stream from step (b).

4. A method according to claim 3, wherein step (c) comprises one of steam stripping and distillation.

5. A method according to claim 3, wherein step (c) comprises steam stripping and the method further comprises the step of using acid from step (c) in step (b).

6. A method according to claim 3, wherein step (c) comprises distillation and the method further comprises the step of using acid from step (c) in step (b).

7. A method according to claim 4, wherein the acidic aqueous solution of step (b) comprises an acid that is volatile under conditions used in the steam stripping or distillation.

8. A method according to claim 1, wherein the acidic aqueous solution of step (b) comprises nitric acid or nitrous acid.

9. A method according to claim 1, wherein step (b) is carried out at a pH of 6 or less.

10. A method according to claim 1, wherein step (b) is carried out at a pH of 5 or less.

11. A method according to claim 1, wherein step (b) is carried out at a pH in the range of 2 to 5.

12. A method according to claim 4, wherein liquid condensed from the top of a steam stripper or a distillation column comprises one or both of nitric acid solution and nitrous acid solution.

13. A method according to claim 12, wherein the condensed liquid comprising one or both of nitric acid solution and nitrous acid solution is used in step (b).

14. A method according to claim 1, wherein step (b) is done in a single stage.

15. A method according to claim 1, wherein step (b) is done in a plurality of stages having a flow pattern that is one of cross-current, counter-current and co-current.

16. A method according to claim 1, wherein the impurities removed in step (b) comprise alkalinity and salt.

17. A method according to claim 2, wherein the water washing or the alkaline washing, or both, are done in a plurality of stages having a flow pattern that is one of cross-current, counter-current and co-current.

18. A method according to claim 1, wherein the nitroaromatic product is one of mononitrobenzene, nitrotoluene and dinitrotoluene.

19. A method according to claim 1, wherein the nitroaromatic product is mononitrobenzene.

20. A method of removing impurities from a product stream comprising a nitroaromatic product, comprising the steps of:
   (a) washing the nitroaromatic product stream with water to remove mineral acids;
   (b) washing the nitroaromatic product stream from step (a) with an acidic aqueous solution to remove hydrophilic acids; and
   (c) removing residual organic reactant from the nitroaromatic product stream from step (b) by one of steam stripping and distillation.

21. A method according to claim 20, wherein step (c) comprises steam stripping and the method further comprises the step of using acid from step (c) in step (b).

22. A method according to claim 20, wherein step (c) comprises distillation and the method further comprises the step of using acid from step (c) in step (b).

23. A method according to claim 20, wherein the acidic aqueous solution of step (b) comprises an acid that is volatile under conditions used in the steam stripping or distillation.

24. A method according to claim 20, wherein the acidic aqueous solution of step (b) comprises nitric acid or nitrous acid.

25. A method according to claim 20, wherein step (b) is carried out at a pH of 6 or less.

26. A method according to claim 20, wherein step (b) is carried out at a pH of 5 or less.

27. A method according to claim 20, wherein step (b) is carried out at a pH in the range of 2 to 5.

28. A method according to claim 20, wherein liquid condensed from the top of a steam stripper or a distillation column comprises one or both of nitric and nitrous acid solution.

29. A method according to claim 28, wherein the condensed liquid is used in step (b).

30. A method according to claim 20, wherein step (b) is done in a single stage.

31. A method according to claim 20, wherein step (b) is done in a plurality of stages having a flow pattern that is one of cross-current, counter-current and co-current.

32. A method according to claim 20, wherein the hydrophilic acids removed in step (b) are used in step (a).

33. A method according to claim 20, wherein the water washing is done in a plurality of stages having a flow pattern that is one of cross-current, counter-current and co-current.

34. A method according to claim 20, wherein the nitroaromatic product is one of mononitrobenzene, nitrotoluene and dinitrotoluene.

35. A method according to claim 20, wherein the nitroaromatic product is mononitrobenzene.

* * * * *